(12) United States Patent
Jain et al.

(10) Patent No.: US 6,755,824 B2
(45) Date of Patent: Jun. 29, 2004

(54) PLATELET INHIBITOR ELUTING ABLATION CATHETER

(75) Inventors: Mudit K. Jain, Woodbury, MN (US); Milton M. Morris, Minneapolis, MN (US); Jeffrey A. Hall, Birmingham, AL (US); Gregory P. Walcott, Wilsonville, AL (US); Bruce KenKnight, Maple Grove, MN (US); David S. Wood, Temecula, CA (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/123,830

(22) Filed: Apr. 15, 2002

(65) Prior Publication Data

US 2003/0195503 A1 Oct. 16, 2003

(51) Int. Cl.[7] .............................................. A61B 18/18
(52) U.S. Cl. ........................................ 606/41; 128/898
(58) Field of Search ...................... 606/20–52; 607/96, 607/98–102, 104

(56) References Cited

U.S. PATENT DOCUMENTS

| | | | |
|---|---|---|---|
| 3,634,123 A | 1/1972 | Eriksson et al. .......... 117/47 A |
| 3,695,921 A | 10/1972 | Shepherd et al. ............. 117/72 |
| 3,844,989 A | 10/1974 | Harumiya et al. ..... 260/17.4 R |
| 3,861,396 A | 1/1975 | Vaillancourt et al. ... 128/350 R |
| 3,935,342 A | 1/1976 | Lim ........................... 427/321 |
| 3,975,350 A | 8/1976 | Hudgin et al. ......... 260/30.4 N |
| 4,026,296 A | 5/1977 | Stoy et al. .................. 128/349 |
| 4,118,485 A | 10/1978 | Eriksson et al. ............ 424/183 |
| 4,145,513 A | 3/1979 | Dalibor ........................ 528/75 |
| 4,267,295 A | 5/1981 | Gallop et al. ................ 526/264 |
| 4,417,892 A | 11/1983 | Meisch ....................... 604/323 |
| 4,434,797 A | 3/1984 | Silander ..................... 128/343 |
| 4,459,317 A | 7/1984 | Lambert ........................ 427/2 |

(List continued on next page.)

OTHER PUBLICATIONS

Cramer et al., "Reduction of Surgical Complication Rate by the Use of a Hypothromogenic Catheter Coating", Radiology 109, pp. 585–588, Dec. 1973.

(List continued on next page.)

*Primary Examiner*—Roy D. Gibson
*Assistant Examiner*—Peter J Vrettakos
(74) *Attorney, Agent, or Firm*—Myers Bigel Sibley & Sajovec

(57) ABSTRACT

An ablation catheter stores a platelet inhibitor substance within a plurality of pockets or recesses of its shaft. The substance is adapted to elute upon contact with biological fluid. In the pocket configuration, the platelet inhibitor substance is in a capsule positioned within the pocket. In the recess configuration, the platelet inhibitor substance is in a hydrogel or silicone-based porous/semi-porous matrix positioned within the recess. Elution of the platelet inhibitor substance prevents or at least substantially minimizes the adhesion of blood platelets on the catheter surface during ablation. In another configuration, the catheter includes an internal lumen network having apertures terminating at the surface of the shaft. The lumen communicates with a source of platelet inhibitor fluid that is forced through the lumen by a variable pump.

22 Claims, 6 Drawing Sheets

U.S. PATENT DOCUMENTS

| | | | |
|---|---|---|---|
| 4,516,970 A | | 5/1985 | Kaufman et al. .......... 604/270 |
| 4,838,876 A | | 6/1989 | Wong et al. ................ 604/265 |
| 5,091,205 A | | 2/1992 | Fan .............................. 427/2 |
| 5,135,516 A | | 8/1992 | Sahatjian et al. ........... 604/265 |
| 5,423,744 A | * | 6/1995 | Gencheff et al. ........... 604/501 |
| 5,531,679 A | * | 7/1996 | Schulman et al. ............ 604/65 |
| 6,475,214 B1 | * | 11/2002 | Moaddeb ..................... 606/41 |

OTHER PUBLICATIONS

Esquivel et al., "Reduced thrombogenic characteristics of expanded polytetrafluoroethylene and polyurethane arterial grafts after heparin bonding", Surgery, vol. 95, No. 1, pp. 102–107, 1983.

Lindhardt et al., "Differential Anticoagulant Activity of Heparin Fragments Prepared Using Microbial Heparinase", The Journal of Biological Chemistry, vol. 257, No. 13, pp. 7310–7313, Jul. 1982.

Miyama et al., "A New Antithrombogenic Heparinized Polymer", J. Biomed. Mater. Res., vol. 11, pp. 251–265, 1977.

Mori et al., "The Effect of Released Heparin From the Heparinized Hydrophilic Polymer (HRSD) on the Process of Thrombus Formation", vol. XXIV Trans. Am. Soc. Artif. Inter. Organs, pp. 736–745, 1978.

Nichols et al., "Effect of heparin bonding on catheter–induced fibrin formation and platelet activation", Circulation, vol. 70, No. 5, pp. 843–850, 1984.

Noishiki et al., "Prevention of Thrombosis–related Complications in Cardiac Catheterization and Angiography Using a Heparinized Catheter (Anthron®)", vol. XXXIII Trans. Am. Soc. Artif. Intern. Organs, pp. 359–365, 1987.

* cited by examiner

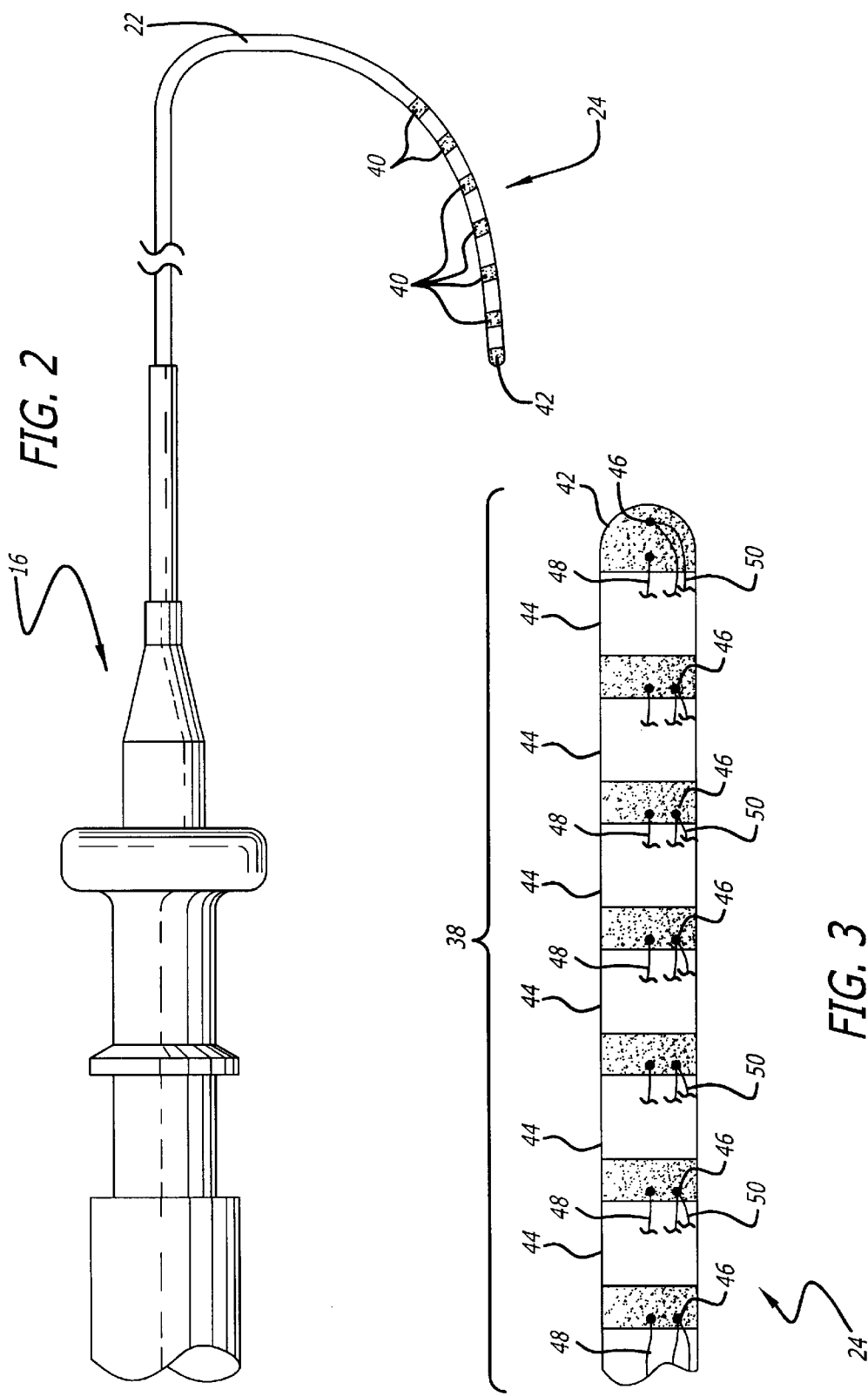

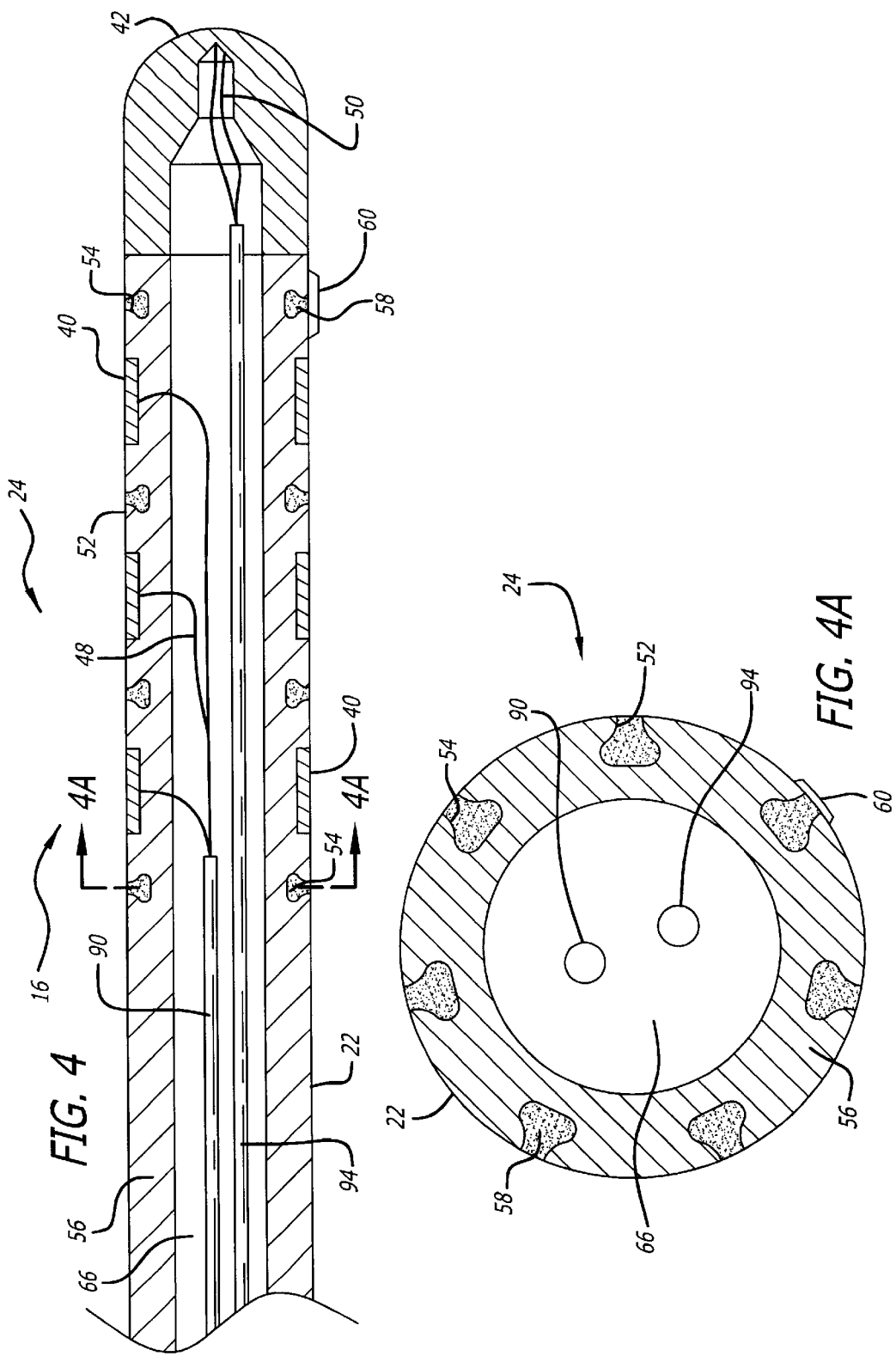

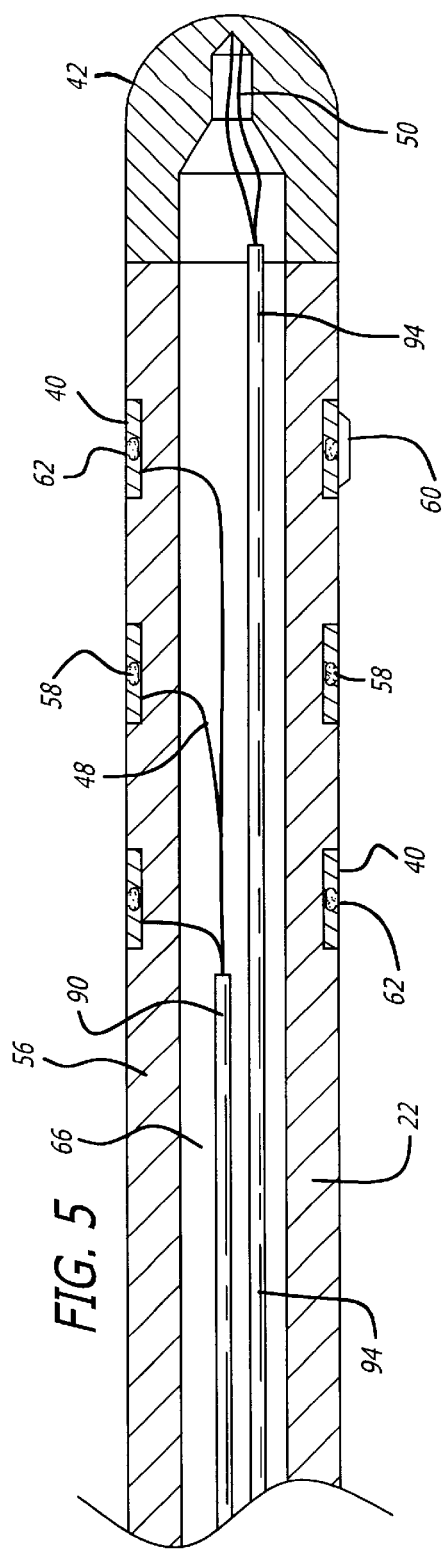
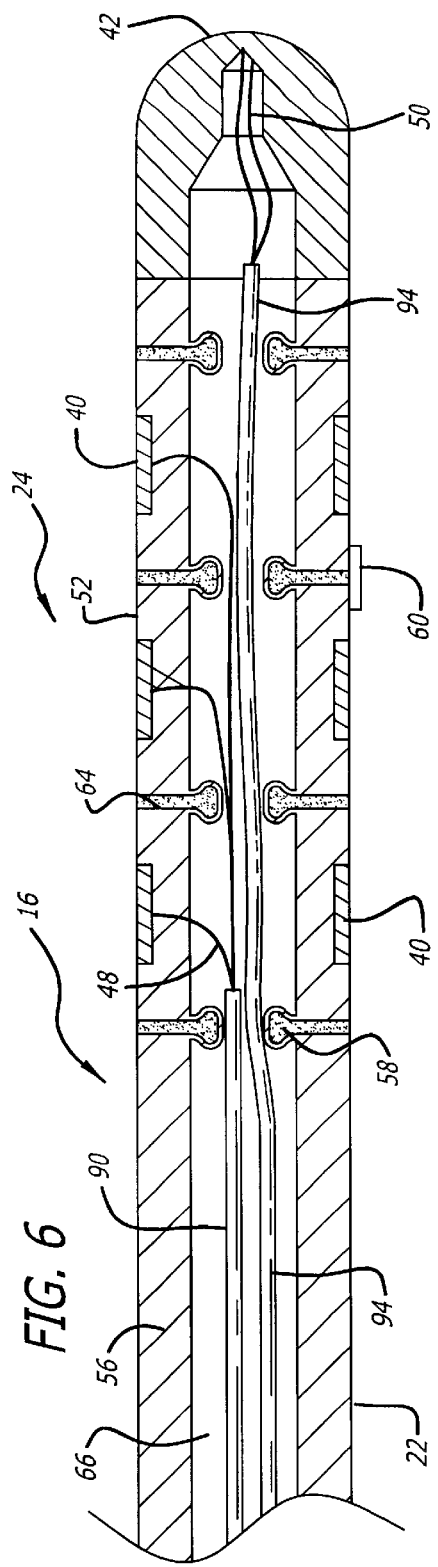

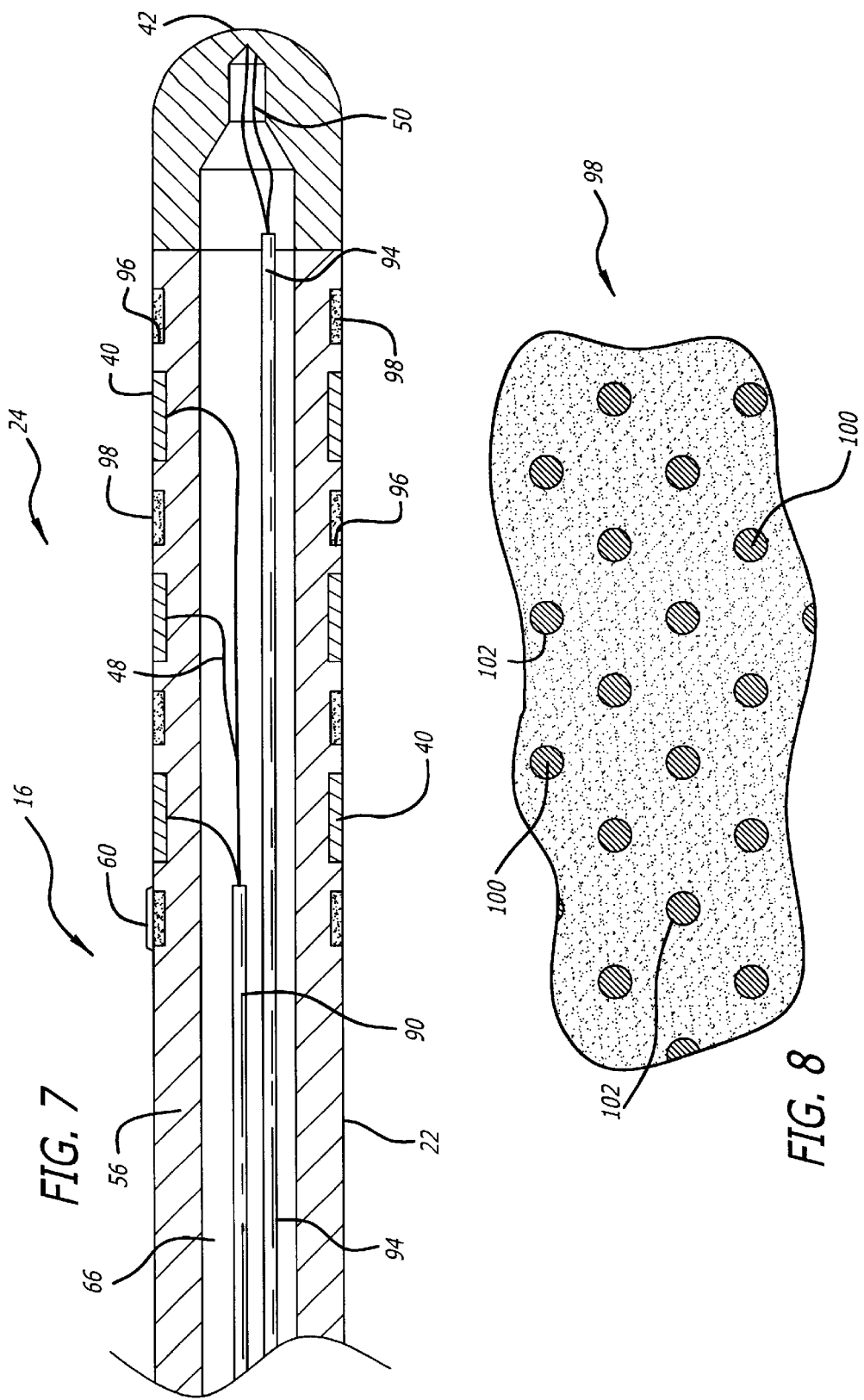

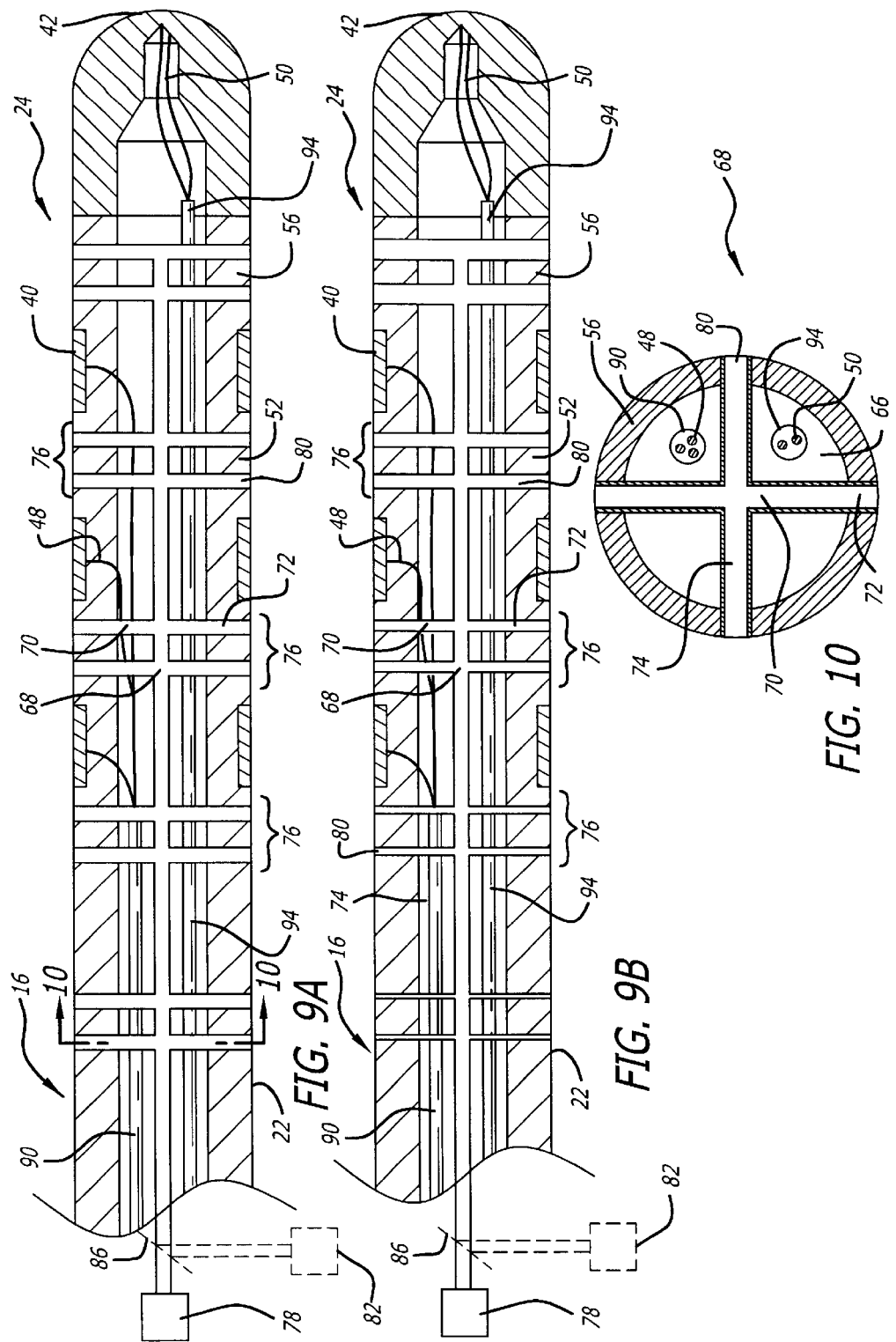

PLATELET INHIBITOR ELUTING ABLATION CATHETER

BACKGROUND OF THE INVENTION

1. Field of the Invention

The invention relates generally to an electrophysiological ("EP") catheter for providing energy to biological tissue within a biological site, and more particularly, to an EP catheter with a platelet inhibitor substance stored therein that becomes eluted upon contact with biological fluid and thereby prevents the formation of coagulum and other substances from adhering to the catheter surface during an ablation procedure.

2. Description of the Related Art

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth, remodeling, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed percutaneously, a procedure in which a catheter is introduced into the patient through an artery or vein and directed to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves the formation of continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. In this therapy, transmural ablation lesions are formed in the atria to prevent atrial reentry and to allow sinus impulses to activate the entire myocardium. In this sense transmural is meant to include lesions that pass through the atrial wall or ventricle wall from the interior surface (endocardium) to the exterior surface (epicardium).

During ablation, RF energy is applied to the electrodes to raise the temperature of the target tissue to a lethal, non-viable state. In general, the lethal temperature boundary between viable and non-viable tissue is between approximately 45° C. to 55° C. and more specifically, approximately 48° C. Tissue heated to a temperature above 48° C. for several seconds becomes permanently non-viable and defines the ablation volume. Tissue adjacent to the electrodes delivering RF energy is heated by resistive heating which is conducted radially outward from the electrode-tissue interface. The goal is to elevate the tissue temperature, which is generally at 37° C., fairly uniformly to an ablation temperature above 48° C., while keeping both the temperature at the tissue surface and the temperature of the electrode below 100° C. In clinical applications, the target temperature is set below 70° C. to avoid coagulum formation. Lesion size has been demonstrated to be proportional to temperature.

Blood coagulation is a major limitation/complication associated with RF ablation therapy. Coagulation can lead to thromboembolism and can also form an insulating layer around the electrode hindering further energy delivery required for ablation therapy. Heat appears to be a major factor in the formation of blood coagulum on a catheter electrode. During a typical RF energy ablation procedure using an EP catheter, on or more electrodes carried by the catheter are positioned such that a portion of the electrodes are in contact with the tissue being ablated while the remaining portion of the electrodes are in contact with blood. The RF energy applied during the procedure resistively heats the tissue which in turn heats the electrode through conduction. As blood stays in contact with the heated electrode, platelet activation occurs. This platelet activation appears to lead to coagulum formation.

Hence, those skilled in the art have recognized a need for providing a catheter with a platelet inhibitor substance dispersed therein that becomes eluted upon contact with biological fluid and thereby prevents the formation of coagulum and other substances from adhering to the catheter surface during an ablation procedure. The invention fulfills these needs and others.

SUMMARY OF THE INVENTION

Briefly, and in general terms, the invention is directed to an ablation catheter having a platelet inhibitor substance dispersed therein that becomes eluted upon contact with biological fluid and thereby prevents the formation of coagulum and other substances from adhering to the catheter surface during an ablation procedure.

In a first aspect, the invention relates to a catheter for use within a body cavity having biological fluid therein. The catheter includes a shaft having a proximal end, a distal-end region and an outside surface. At least one pocket is carried by the shaft and has an opening terminating at the outside surface of the shaft. The catheter also includes a soluble platelet inhibitor substance within the at least one pocket that is adapted to pass through the pocket opening upon contact with the biological fluid. By incorporating a platelet inhibitor substance within the pocket opening for the subsequent elution thereof, adhesion of blood platelets on the surface of the catheter is prevented or at least substantially minimized. Accordingly, coagulum causing components of the blood cannot contact the catheter surface and coagulation cannot begin and hence, not propagate.

In a detailed aspect, the platelet inhibitor includes heparin, glycoprotein IIb/IIIa inhibitor and aspirin. In another detailed aspect, the shaft has a tubular wall which carries the at least one pocket. In yet another detailed aspect, the at least one pocket is within the tubular wall. In a further detailed aspect, the at least one pocket is within the lumen defined by the tubular wall. In another detailed aspect, the shaft further includes at least one electrode that carries the at least one pocket. In other detailed aspects, a layer of a platelet inhibitor substance is posited on an outside surface of the shaft. Alternatively, a layer of a heparin and sugar-based solution mixture is deposited over the outside surface of the shaft with the layer adapted to dissolve into the biological fluid. In a further detailed aspect, the solubility of the platelet inhibitor substance increases with temperature through application of RF energy by an RF generator to the catheter surface.

In a second aspect, the invention relates to a catheter system for use within a body cavity. The catheter system includes a shaft having a proximal end and a distal-end region. The shaft carries a lumen network having a proximal opening that communicates with a source of platelet inhibitor solution and at least one distal opening that is adapted to terminate at the outside surface of the shaft. The catheter system further includes a first mechanism adapted to force the platelet inhibitor solution from the source through the at least one distal opening of the lumen network. The distal-end region of the shaft carries a plurality of electrodes.

In a detailed aspect, the platelet inhibitor includes heparin, glycoprotein IIb/IIIa inhibitor and aspirin. In another detailed aspect, the distal-end region of the shaft includes an aperture and the distal-opening of the lumen network terminates at the outside surface of the shaft through the aperture. In still another detailed aspect, the aperture is carried by one of the electrodes. In a further detailed aspect, the lumen network includes a central lumen extending along the length of the shaft, and a plurality of branch lumens communicating with the central lumen at a first end and terminating at the outside surface of the shaft at a second end.

In another detailed aspect, the shaft includes a plurality of apertures, each coincident with one of the branch-lumen second ends. In yet another detailed aspect, the apertures are the same size. In still another detailed aspect, the apertures decrease in size progressively along the length of the shaft from the most distal aperture to the most proximal aperture. In a further detailed aspect, at least one of the plurality of apertures is carried by one of the electrodes. In yet a further detailed aspect, each pair of adjacent electrodes has at least one of the plurality of apertures located therebetween.

In another detailed aspect, the first mechanism is adapted to control the flow rate of the platelet inhibitor solution through the lumen network when in an "on" position and to prevent the flow of platelet inhibitor solution when in an "off" position. In still another detailed aspect, the first mechanism includes a first variable pump located between the platelet-inhibitor-solution source and the proximal end of the lumen network. In a further detailed aspect, the proximal opening of the lumen network also communicates with a source of saline solution and the catheter further includes a second mechanism adapted to force the saline solution from the source through the at least one distal opening of the lumen network when the first mechanism is in an "off" position. In another detailed aspect, the second mechanism includes a second variable pump located between the saline solution source and the proximal end of the lumen network. In yet another detailed aspect, the second variable pump controls the flow rate of the saline solution through the lumen network. In still another detailed aspect, the catheter further includes a flow valve attached to the first and second variable pumps and adapted to switch between the first and second variable pumps.

In a third aspect, the invention relates to a catheter for use within a body cavity having biological fluid therein. The catheter includes a shaft having a proximal end, a distal-end region, and at least one recess on its outside surface. A soluble platelet inhibitor substance is located within the at least one recess and is adapted to elute upon contact with the biological fluid.

In a detailed aspect, the platelet inhibitor includes heparin, glycoprotein IIb/IIIa inhibitor, and aspirin. In another detailed aspect, the platelet inhibitor is dispersed within a matrix. In yet another detailed aspect, the matrix includes one of a porous matrix and a semi-porous matrix. In a further detailed aspect, the matrix consists of silicone. In another detailed aspect, the matrix includes a hydrogel. In still another detailed aspect, the hydrogel is selected from the group of polymers including polyacrylamide, polyvinyl pyrolidone, polyhydroxyethal methacrylate and polyvinyl alcohol. In a further detailed aspect, the catheter includes a layer of a heparin and a sugar-based solution mixture posited over the platelet inhibitor substance, the layer adapted to dissolve into the biological fluid. In a yet further detailed aspect, the catheter includes at least one electrode at the distal-end region of the shaft wherein the at least one recess is located on the outside surface of the at least one electrode. In another detailed aspect, the solubility of the platelet inhibitor substance increases with temperature through application of RF energy by an RF generator.

In a fourth aspect, the invention relates to a method of applying energy to biological tissue within a biological site. The method involves positioning a catheter having at least one electrode, and at least one pocket carried by the catheter having an opening terminating at the outside surface of the catheter, the pocket filled with a platelet inhibitor substance, within the biological site so that the electrode is adjacent the tissue to be ablated. RF energy is applied to the at least one electrode.

In a detailed aspect, the catheter has at least one pocket carried by a tubular wall of the catheter. In another detailed aspect, the at least one pocket is within the tubular wall. In still another detailed aspect, the at least one pocket is within the lumen defined by the tubular wall. In a further detailed aspect, the at least one pocket is carried by the at least one electrode.

In a fifth aspect, the invention relates to a method of applying energy to biological tissue within a biological site using a catheter having at least one electrode, and a lumen network carried by the shaft and having a proximal opening communicating with a source of platelet inhibitor solution and at least one distal opening terminating at an outside surface of the shaft. The method involves positioning the catheter within the biological site so that the electrode is adjacent to the tissue to be ablated. Energy is applied to the electrode while the platelet inhibitor solution is forced from the source through the at least one distal opening of the lumen network.

In a detailed aspect, the forcing of platelet inhibitor solution occurs during the application of energy. In another detailed aspect, the proximal opening of the lumen network communicates with a source of saline solution. The saline solution is forced from the source through the at least one distal opening of the lumen network. In yet another detailed aspect, the forcing of the saline solution occurs during the positioning of the catheter. In a further detailed aspect, the application of energy occurs intermittently within a time period having positions of "on" power and "off" power periods wherein the forcing of saline solution occurs during "off" periods and the forcing of platelet inhibitor occurs during "on" periods.

In a sixth aspect, the invention relates to a method of applying energy to biological tissue within a biological site. The method involves positioning a catheter having at least one electrode, and at least one recess carried by the catheter having an opening terminating at the outside surface of the catheter, the recess filled with a matrix having a platelet inhibitor substance dispersed therein. The catheter is positioned within the biological site so that the electrode is adjacent the tissue to be ablated. As energy is being applied to the at least one electrode, the platelet inhibitor substance is released from the at least one recess for eluting the platelet inhibitor substance within a biological fluid.

In a detailed aspect, the platelet inhibitor substance is eluted in the biological fluid after released from its stored position in a recess. In another detailed aspect, the matrix is a porous/semi-porous silicone. In a further detailed aspect, the platelet inhibitor substance is uniformly dispersed in a porous/semi-porous hydrogel matrix. In a still further detailed aspect, elution of the platelet inhibitor occurs when the biological fluid contacts the matrix.

These and other aspects and advantages of the invention will become apparent from the following detailed description and the accompanying drawings, which illustrate by way of example the features of the invention. These and other aspects and advantages of the invention will become apparent from the following detailed description and the accompanying drawings, which illustrate by way of example the features of the invention.

BRIEF DESCRIPTION OF THE DRAWINGS

FIG. 2 is a diagram of the catheter system of FIG. 1 presenting more detail including a handle and a catheter shaft having a preformed distal segment carrying a linear array of electrodes having a surface covering.

FIG. 3 is a detailed schematic block diagram of a portion of the distal segment of the catheter system of FIG. 2, depicting a tip electrode and several band electrodes.

FIG. 4 is across-section view of the distal-end region of a catheter shaft configured in accordance with the invention depicting a series of pockets positioned between adjacent electrodes for storing a platelet inhibitor substance.

FIG. 4A is a transverse cross-section of the distal-end region of the shaft of FIG. 4, taken along the line 4A—4A respectively, depicting a series of pockets positioned around the outside circumference of the shaft.

FIG. 5 is a cross-section view of the distal-end region of the shaft configured in accordance with the invention depicting a series of pockets embedded within a plurality of electrode bands for storing the platelet inhibitor substance.

FIG. 6 is a cross-section view of the distal-end region of the shaft configured in accordance with the invention depicting a series of elongated pockets positioned between adjacent electrodes and extending into the inner lumen of the shaft for storing the platelet inhibitor substance.

FIG. 7 is a cross-section view of the distal-end region of the shaft configured in accordance with the invention depicting a series of recesses containing porous or semi-porous matrices with platelet inhibitor substance dispersed therein and positioned flush to the outer surface of the shaft.

FIG. 8 is a close-up, flattened view of a porous or semi-porous matrix with a platelet inhibitor substance dispersed therein.

FIG. 9A is a cross-section view of the distal-end region of the shaft configured in accordance with the invention depicting a first mechanism and a combination of the first mechanism and a second mechanism (shown in broken lines) for forcing the platelet-inhibitor solution through a lumen network of the shaft.

FIG. 9B is a cross-section view of the distal-end region of the shaft configured in accordance with the invention depicting a plurality of apertures which decrease in size progressively along the length of the shaft from the most distal aperture to the most proximal aperture.

FIG. 10 is a transverse cross-section of the lumen network within the shaft of FIG. 9A, taken along the line 10—10 respectively.

DETAILED DESCRIPTION OF THE PREFERRED EMBODIMENTS

Figure 1:
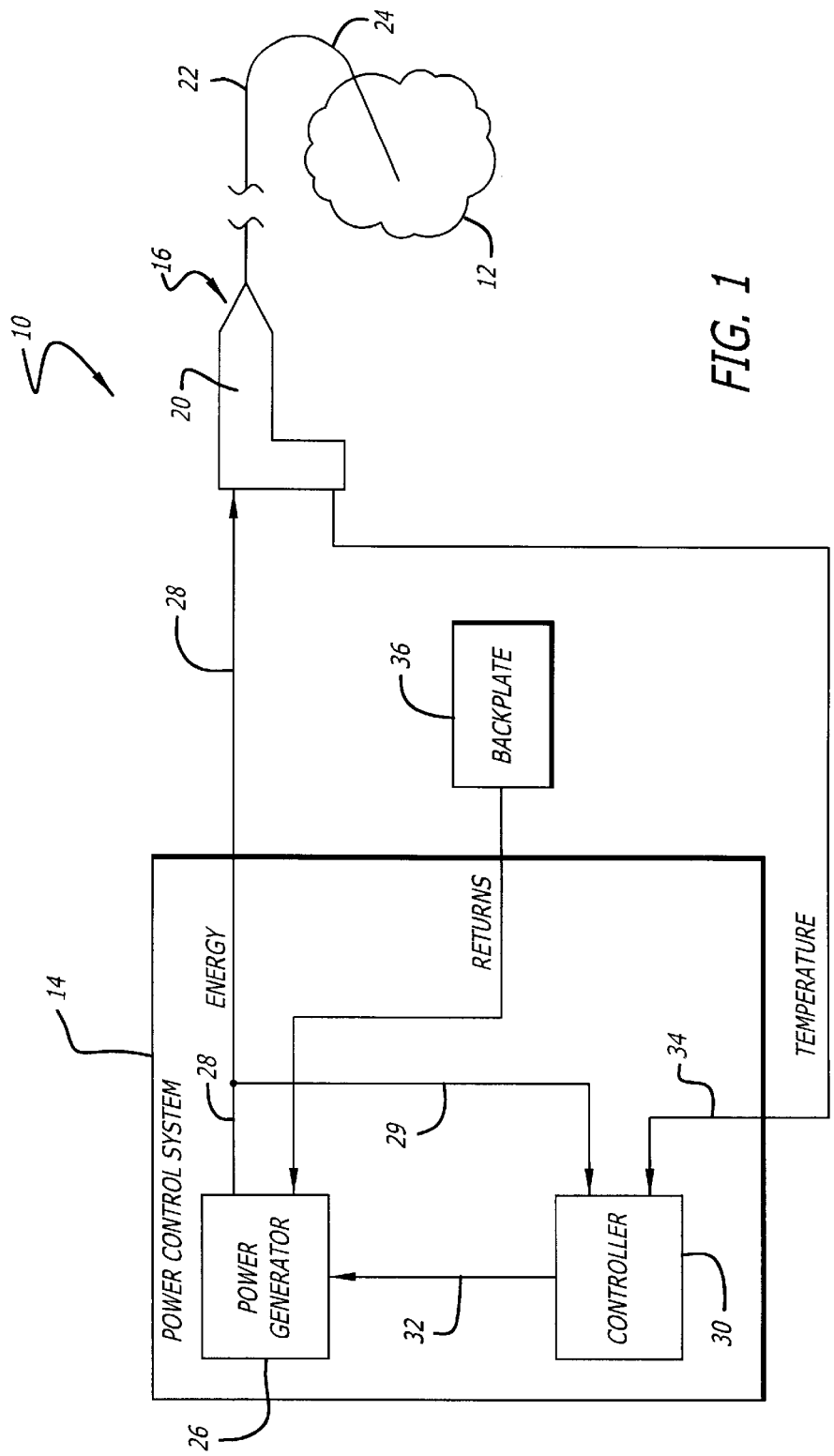
FIG. 1 is a schematic block diagram of an ablation system including a power control system ("PCS") and a catheter system configured in accordance with aspects of the invention.

Turning now to the drawings, in which like reference numerals are used to designate like or corresponding elements among the several figures, in FIG. 1 there is shown a system 10 for use in ablation therapy of a biological site 12, e. g., the atrium or ventricle of the heart. The system 10 includes a power control system 14 and a catheter system 16. The catheter system 16 includes a handle 20 and a steerable catheter shaft 22 having a distal-end region 24. The distal-end region 24 carries an electrode system (not shown) and is capable of being percutaneously introduced into a biological site.

The power control system 12 includes a power generator 26, that may have any number of output channels through which it provides power 28 to the catheter system 16. The operation of the power generator 26 is controlled by a controller 30 which outputs control signals 32 to the power generator 26. The controller 30 monitors the power 28 provided by the power generator 26 along a power monitor line 29. In addition, the controller 30 also receives temperature signals 34 from the catheter system 16. Based on the power 28, and the temperature signals 34 the controller 30 adjusts the operation of the power generator 26.

The system 10 may further include a backplate 36. The backplate 36 is connected to the power generator 26 and generally provides a return path for the power 28 delivered to the biological site 12 through the catheter system 16.

As shown in FIGS. 2 and 3, the distal-end region 24 of the catheter system 16 includes an electrode system 38 (FIG. 3). The electrode system 38 is shown in schematic form with the components drawn in more detail to more clearly illustrate the relationship between the components. A preferred embodiment of the electrode system 38 includes twelve band electrodes 40 arranged in a substantially linear array along the distal segment 24 of the catheter sheath 22. The electrode system 38 may include a tip electrode 42. For clarity of illustration, only four band electrodes 40 are shown in FIG. 3 although as stated, a preferred embodiment may include many more. The band electrodes 40 are arranged so that there is space 44 between adjacent electrodes. In one configuration of the electrode system 38, the width of the band electrodes 40 is 3 mm and the space 44 between the electrodes is 4 mm. The total length of the electrode system 38, as such, is approximately 8 cm.

The arrangement of the band electrodes 40 is not limited to a linear array and may take the form of other patterns such as circular and curvilinear arrays. A substantially linear array is preferred for certain therapeutic procedures, such as treatment of atrial fibrillation, in which linear lesions of typically 4 to 8 cm in length are desired. A linear array is more easily carried by the catheter shaft 22 and also lessens the size of the catheter.

The band electrodes 40 and tip electrode 42 are formed of a material having a significantly higher thermal conductivity than that of the biological tissue to be ablated. Possible materials include silver, gold, chromium, aluminum, molybdenum, tungsten, nickel, platinum, and platinum/10% iridium. Because of the difference in thermal conductivity between the electrodes 40, 42 and the tissue, the electrodes cool off more rapidly in the flowing fluids at the biological site. The band electrodes 40 are sized so that the surface area available for contact with fluid in the heart, e.g., blood, is sufficient to allow for efficient heat dissipation from the electrodes to the surrounding blood. In a preferred embodiment, the electrodes 40 are 7 French (2.3 mm in diameter) with a length of 3 mm and a thickness in the range of about 0.002 mm to about 0.010 mm.

Associated with the electrode system 38 are thermal sensors 46 for monitoring the temperature of the electrode system 38 at various points along its length. In one embodiment, each electrode 40, 42 has a thermal sensor 46 mounted to it. Each thermal sensor 46 provides a temperature signal 34 (FIG. 1) to the controller 30 which is indicative of the temperature of the respective band electrode 40 (FIGS. 2 and 3) at that sensor. In another embodiment of the electrode system 38 a thermal sensor 46 is mounted on every other band electrode 40. Thus for a catheter having twelve electrodes, there are thermal sensors on six electrodes. In yet another embodiment of the electrode system 38, every other electrode has two thermal sensors 46. In FIG. 3, which shows an embodiment having one thermal sensor for each electrode, there is shown a single power lead 48 for each electrode 40 to provide power to each electrode for ablation purposes and two temperature leads 50 for each thermal sensor 46 to establish a thermocouple effect.

In accordance with the present invention, the distal-end region 24 of the shaft 40 is configured to elute a platelet inhibitor substance into the blood during ablation therapy of the biological site 12. Experimentation has shown that elution of the platelet inhibitor substance 58 during or immediately prior to ablation significantly reduces the risk of blood coagulation since the temperature at which blood coagulum occurs is raised in platelet inhibitor-fortified blood.

With reference to FIGS. 4 and 4A, in one embodiment of the invention, positioned along the outside surface 52 of the shaft 22 and between adjacent band electrodes 40 are a series of small pockets 54 carried by the shaft. In a preferred embodiment, the size of the pockets 54 range from 0.5 mm to 2 mm in length. The series of small pockets 54 are formed within a tubular wall 56 of the shaft 40 with each pocket having an opening that terminates at the outside surface 52 of the shaft. These pockets 54 can be formed by drilling holes through the surface of the shaft 40. Stored within each of the series of pockets 54 is a platelet inhibitor substance 58. The platelet inhibitor substance 58 is deposited in the pockets under pressure using an extrusion process and is adapted to pass through the pocket opening upon contact with biological fluid (not shown). The extrusion process involves the use of a larger metal tube with one end placed around the pocket 54 on the outside surface 52 of the shaft 40 to enable the extrusion of the platelet inhibitor substance 58 (in the form of a tablet-like capsule) through the tube under pressure into each respective pocket 54.

A pressure molding press can be used to compress the platelet inhibitor substance 58 to form the tablet-like capsule of 100% drug that will start eluting on contact with the blood. Alternatively, the platelet inhibitor substance and starch/manitol can be pressure molded into a desired shape to fill the series of pockets 54 positioned along the shaft. The addition of starch/manitol causes the platelet inhibitor substance to dissolve at a slower rate than the 100% drug capsule. Another way to slow the solubility rate of the platelet inhibitor substance in the blood involves esterfication, a chemical interaction with an ether or alcohol, of the anti-platelet substance. One other possible way to slow the solubility rate of the platelet inhibitor substance in the blood is to mix the platelet inhibitor substance with polymeric binders (i.e., silicone, polyurethane, polyethylene). The polymeric binder is dissolved in THF (tetra hydro furan-high vapor pressure) and then the platelet inhibitor substance is added to the solution. The high vapor pressure of THF causes it to evaporate, leaving the drug in a polymeric binder. The platelet inhibitor substance 58 elutes or dissolves upon contact with biological fluid due to the concentration differential between the inside of the pocket 54 and the outside of the shaft 40 surrounded by biological fluid. Exemplary of preferred fast-acting platelet inhibitors for use in the present invention include heparin, glycoprotein IIb/IIIa inhibitor, and aspirin.

FIG. 4A represents a transverse cross-section of the distal-end region 24 of the shaft 22 of FIG. 4 taken along the line 4A—4A respectively, depicting an arrangement of the series of small pockets 54 around the outside circumference of the shaft.

During an ablation procedure, the distal-end region 24 of the catheter is positioned within a body cavity 12 (FIG. 1) having biological fluid, e.g., blood, flowing through. The platelet inhibitor substance 58 within the pockets 54 comes in contact with the blood and dissolves into the blood through the pocket openings. On contact with the biological fluid the platelet inhibitor substance 58 elutes. As the catheter is heated by power generator means, the source of heat from each respective electrode 40 is transferred over to the pockets 54 positioned between the electrodes along the catheter surface.

With regard to the relationship between the solubility of the platelet inhibitor capsule 58 and the temperature from application of RF energy, the solubility of the platelet inhibitor substance generally increases with temperature. As the catheter is heated during an ablation procedure, the platelet inhibitor capsule 58 becomes porous allowing the biological fluid into the core of the capsule. Accordingly, the platelet inhibitor absorbs the biological fluid and increases in size which creates cracks in the capsule 58 thereby causing the elution rate to increase with temperature. This procedure enables more of the platelet inhibitor substance to be eluted than during other phases of the ablation procedure, such as the placement of the catheter in the biological site.

Referring to FIG. 5, in another embodiment of the invention, a series of small pockets 62 are formed within each band electrode 40. These series of small pockets 62 can be formed by drilling a hole through the surface of each band electrode 40. Accordingly, each of the pockets 62 has an opening terminating at the outside surface of its respective electrode band 40. Stored within each of the pockets 62 is a platelet inhibitor substance 58. The platelet inhibitor substance 58 is deposited in the pockets under pressure using an extrusion process as described above. During an ablation procedure using the embodiment of the invention, the distal-end region 24 of the catheter is positioned within a body cavity 12 (FIG. 1) having biological fluid, e.g., blood, flowing through. RF energy is applied to the electrodes 40 by the RF generator 26 (FIG. 1). The platelet inhibitor substance 58 within the pockets 62 comes in contact with the blood and dissolves into the blood through the pocket openings. As the platelet inhibitor substance 58 passes through the pocket 62 opening, it becomes eluted or dissolved upon contact with biological fluid (not shown) within the body cavity (not shown).

As shown in FIG. 6, in another embodiment of the invention, a series of elongated pockets 64 are positioned between adjacent electrodes 40 along the distal-end region 24 of the shaft 22. The elongated pockets 64 pass through the tubular wall 56 and extend into an inner lumen 66 of the shaft 22 defined by the tubular wall. Each pocket 64 has an opening that terminates at the outside surface 52 of the shaft 22. Stored inside each of the pockets 64 is a platelet inhibitor substance 58 which passes through the pocket opening upon contact with biological fluid (not shown). On contact with the biological fluid the platelet inhibitor substance 58 elutes.

With reference to FIG. 7, in another embodiment of the invention, a series of small recesses 96 are positioned between adjacent electrodes 40 along the distal-end region 24 of the shaft 22. The series of small recesses 96 are slightly embedded within the tubular wall 56 of the shaft 22. A porous or semi-porous matrix 98 is positioned within the recess 96 such that it is flush with the outside surface 52 of the shaft 22. The platelet inhibitor substance 100 is evenly dispersed within the silicone-based porous or semi-porous matrix 98. Elution of the platelet inhibitor substance 100 occurs when the silicone-based matrix 98 comes into contact with the biological fluid.

One type of porous or semi-porous matrix that can be used in the present invention employs a mixture of the platelet inhibitor substance 100 with silicone in a liquid form (MDX-4-4210 and 6860, Dow Corning). The mixture consists of a toothpaste-like consistency and can be used to fill the recesses 96 positioned along the shaft 22. Alternatively, hydrogels such as polyacrylamide, polyvinylpyrolidone, polyhydroxyethal methacrylate, or polyvinyl alcohol can be used in addition to silicone to form a porous or semi-porous matrix. The aforementioned types of hydrogels are hydrophilic and allow for moisture to absorb therein. The silicone or hydrogel-based matrix is placed into the recesses 96 under pressure using the same extrusion process as described above.

Regarding the relationship between the solubility of the platelet inhibitor substance 58 and the temperature from the application of RF energy, the solubility of the platelet inhibitor substance typically increases with temperature. As the catheter is heated during an ablation procedure, the hydrogel matrix becomes more porous and allows the biological fluid into the core of the hydrogel-platelet inhibitor capsule. Accordingly, the platelet inhibitor absorbs the fluid and increases in size which creates cracks in the hydrogel capsule thereby causing the elution rate to increase with temperature. It is this procedure which enables more of the platelet inhibitor substance to be eluted during an ablation procedure than during other phases of the procedure, e.g., placement of the catheter in the biological site.

FIG. 8 illustrates a close-up, flattened view of a porous or semi-porous matrix 98 with the platelet inhibitor substance 100 dispersed therein. The pores 102 of either a porous or semi-porous matrix 98 are formed evenly throughout the matrix. The matrix 98 may be configured to assume a variety of different shapes so long as the recesses 96 are entirely covered and the matrix is flush to the outside surface 52 of the shaft 22. Exemplary of the various shapes that may be assumed by the matrix include among others, longitudinal grooves, V-shapes, inverted V-shapes, and extrusion pockets (not shown).

To control the rate of elution during the introduction of the catheter into a body cavity (not shown), a thin layer of a mixture of heparin and a sugar-based solution 60 may be deposited over the platelet inhibitor substance 58, as shown in FIGS. 4–7. Preferably, the proportion of the mixture of heparin to the sugar-based solution is less than 10% heparin. Even though FIGS. 4–7 illustrate the layer of the heparin/sugar-based solution mixture applied only to one pocket, electrode, or recess, the heparin/sugar-based solution is not limited to such, and may be applied to all of the pockets, electrodes, or recesses embedded within the catheter shaft 40. The layer of the heparin/sugar-based solution is adapted to dissolve upon contact with the biological fluid. In an alternate configuration of this embodiment, a layer (not shown) of the platelet inhibitor substance 58 may be deposited on the entire outside surface 52 of the shaft with a thin layer of the heparin/sugar-based solution 60 mixture placed thereon.

Referring to FIG. 9A, in another embodiment of the invention, the catheter 10 includes a shaft 22 having a distal-end region 24, a proximal end (not shown), a lumen network 68, and a plurality of electrodes 40 positioned along the distal-end region 24 of the shaft 22. The lumen network 68 is carried by the shaft 22 and has a proximal opening 70 communicating with a source of platelet inhibitor solution (not shown) and a plurality of distal openings 72 adapted to terminate at the outside surface 52 of the shaft 22. The lumen network 68 includes a central lumen 74 spanning the length of the shaft 22, and a plurality of branch lumens 76 communicating with the central lumen at a first end and terminating at the outside surface 52 of the shaft 22 at a second end. In a preferred embodiment, a first mechanism 78 is adapted to force the platelet inhibitor solution from the source through the distal openings 72 of the lumen network 68. The first mechanism, consisting of a first variable pump 78 (model 7518-010, Cole Palmer, Barrington, Ill.), is adapted to control the flow rate of the platelet-inhibitor solution through the lumen network when in an "on" position and to prevent the flow of platelet-inhibitor-solution when in an "off" position. The first variable pump 78 is located between the platelet-inhibitor solution source and the proximal end of the lumen network. Alternatively, other types of pumps can be used as the first mechanism which include a syringe pump and an IV pressure bag with a pressure cuff.

With continued reference to FIG. 9A, the distal-end region 24 of the shaft 22 includes a plurality of apertures 80 in which the distal openings 72 of the lumen network 68 terminate at the outside surface 52 of the shaft 22 through the aperture. Alternatively, the aperture 80 may be carried by one of the band electrodes 40 on the distal-end region 24 of the shaft 22. As shown in FIG. 9A, the shaft 22 includes a plurality of apertures 80, each coincident with one of the branch lumen 76 second ends, wherein the apertures 80 are the same size.

In another embodiment, shown in FIG. 9B, the apertures 80 decrease in size progressively along the length of the shaft 22 from the most distal aperture to the most proximal aperture. The difference in size among the apertures 80 along the length of the shaft 22 ensures that the platelet inhibitor solution reaches the distal electrodes rather than being drained entirely through the proximal electrodes first before reaching the distal electrodes. Each pair of adjacent electrodes 40 may have at least one of the plurality of apertures 80 located therebetween.

Referring to FIG. 9A, in another embodiment of the invention, the proximal opening 70 of the lumen network 68 also communicates with a source of saline solution (not shown). A second mechanism 82 (shown in broken lines) is adapted to force the saline solution from the source through the distal opening 72 of the lumen network 68 when the first mechanism is in an "off" position. The second mechanism, consisting of a second variable pump 82 (model 7518-010, Cole Palmer, Barrington, Ill.), is adapted to control the flow rate of the saline solution through an offset lumen 78 leading into the central lumen 74 of the lumen network 68. The second variable pump 82 is located between the saline solution source and the proximal end (not shown) of the lumen network 68. Using the second variable pump 82 to pump saline solution through the lumen network 68 prevents the apertures 80 or distal openings 72 of the lumen network 68 from getting plugged by the biological fluid so that platelet-inhibitor solution may be efficiently delivered when elution is necessary. A flow valve 86 (shown in broken lines) is attached to the first and second variable pumps 78, 82 and is adapted to switch between the first and second variable pumps.

FIG. 10 depicts a transverse cross-section of the shaft 22 with the lumen network 68 of FIG. 9A, taken along the line 10—10 respectively. A sheath 90 for carrying the feed wires 48 is positioned on one side of the central lumen 74 and is opposite a sheath 94 for carrying the pair of thermocouple wires 52. Shown in FIG. 10 is a cross-section of the proximal opening 70 and distal opening 72 of the lumen network 68.

During an ablation procedure using the embodiments shown in FIGS. 9A–10, the distal-end region 24 is guided through a patient's vascular system. The second variable pump 82, during this time, is turned on such that saline solution is forced through the lumen network 68. Once the distal-end region 24 is within the biological site and properly positioned for ablation therapy, the second variable pump 82 is shut off and the first variable pump 78 is turned on such that platelet inhibitor solution is forced through the lumen network 68. The flow valve 86 attached to the first and second variable pumps 78, 82 facilitates the switching between the first and second variable pumps. RF energy is applied to the electrodes 40,42 during this time. Elution of the platelet inhibitor solution occurs as the platelet inhibitor solution is released from the distal opening 72 of the lumen network 68 through a plurality of apertures 80 positioned along the distal-end region 24 of the catheter and comes into contact with biological fluid.

It will be apparent from the foregoing that, while particular forms of the invention have been illustrated and described, various modifications can be made without departing from the spirit and scope of the invention.

What is claimed is:

1. A method of applying energy to biological tissue within a biological site having biological fluid therein, said method comprising:
    positioning a catheter having at least one electrode and at least one pocket having a length from about 0.5 mm to about 2 mm carried by die catheter and having an opening terminating at the outside surface of the catheter, within the biological site so that the electrode is adjacent the tissue to be ablated; and
    applying RF energy to the at least one electrode;
    wherein the pocket is filled with a platelet inhibitor substance adapted to elute upon contact with the biological fluid.

2. The method of claim 1 wherein the at least one pocket is carried by a tubular wall of the catheter.

3. The method of claim 2 wherein the at least one pocket is within the tubular wall.

4. The method of claim 2 wherein the at least one pocket is within the lumen defined by the tubular wall.

5. The method of claim 1 wherein the at least one pocket is carried by the at least one electrode.

6. The method of claim 1 further comprising depositing the platelet inhibitor substance in the pockets under pressure using an extrusion process.

7. The method of claim 1 wherein the platelet inhibitor substance comprises a tablet-like capsule.

8. The method of claim 7 wherein the tablet-like capsule comprises 100% of a platelet inhibitor drug.

9. The method of claim 1 wherein the at least one pocket comprises an elongate aperture.

10. The method of claim 1 wherein the at least one pocket comprises a plurality of pockets each having an aperture, the apertures for the plurality of pockets being substantially the same size.

11. The method of claim 1 wherein the at least one pocket comprises a plurality of pockets each having an aperture, the apertures for the plurality of pockets decreasing in size along the length of the catheter.

12. The method of claim 1 further comprising depositing a layer of a mixture of heparin and sugar-based solution over the platelet inhibitor substance.

13. A method of applying energy to biological tissue within a biological site having biological fluid therein, said method comprising:
    positioning a catheter having at least one electrode and at least one recess having a length from about 0.5 mm to about 2 mm carried by the catheter and having an opening terminating at the outside surface of the catheter, within the biological site so that the electrode is adjacent the tissue to be ablated; and
    applying energy to the at least one electrode;
    wherein the recess is filled with a matrix having a platelet inhibitor substance dispersed therein that is adapted to elute upon contact with the biological fluid.

14. The method of claim 13 wherein the matrix is a porous/semi-porous silicone.

15. The method of claim 13 wherein the platelet inhibitor substance is uniformly dispersed in a porous/semi-porous hydrogel matrix.

16. The method of claim 13 further comprising depositing the platelet inhibitor substance in the recess under pressure using an extrusion process.

17. The method of claim 13 wherein the platelet inhibitor substance comprises a tablet-like capsule.

18. The method of claim 17 wherein the tablet-like capsule comprises 100% of a platelet inhibitor drug.

19. The method of claim 13 wherein the at least one recess comprises an elongate aperture.

20. The method of claim 13 wherein the at least one recess comprises a plurality of recesses each having an aperture, the apertures for the plurality of recesses being substantially the same size.

21. The method of claim 13 wherein the at least one recess comprises a plurality of recesses each having an aperture, the apertures for the plurality of recesses decreasing in size along the length of the catheter.

22. The method of claim 13 further comprising depositing a layer of a mixture of heparin and sugar-based solution over the platelet inhibitor substance.

* * * * *

UNITED STATES PATENT AND TRADEMARK OFFICE
CERTIFICATE OF CORRECTION

PATENT NO.   : 6,755,824 B2
DATED        : June 29, 2004
INVENTOR(S)  : Jain et al.

It is certified that error appears in the above-identified patent and that said Letters Patent is hereby corrected as shown below:

<u>Column 11,</u>
Line 60, should read -- about 2 mm carried by the catheter and having an --

Signed and Sealed this

Ninth Day of November, 2004

JON W. DUDAS
*Director of the United States Patent and Trademark Office*